US010316482B2

(12) United States Patent
Hoekstra

(10) Patent No.: US 10,316,482 B2
(45) Date of Patent: Jun. 11, 2019

(54) SOIL PROBING DEVICE HAVING A STRING OF FLEXIBLY CONNECTED ROD SECTIONS

(71) Applicant: A.P. van den Berg Holding B.V., Heerenveen (NL)

(72) Inventor: Arend Tjeerd Hoekstra, Heerenveen (NL)

(73) Assignee: A.P. van den Berg Holding B.V., Heerenveen (NL)

(*) Notice: Subject to any disclaimer, the term of this patent is extended or adjusted under 35 U.S.C. 154(b) by 6 days.

(21) Appl. No.: 15/099,785

(22) Filed: Apr. 15, 2016

(65) Prior Publication Data

US 2016/0305081 A1 Oct. 20, 2016

(30) Foreign Application Priority Data

Apr. 17, 2015 (NL) ...................................... 2014659

(51) Int. Cl.
*E02D 1/02* (2006.01)
*F16L 37/244* (2006.01)
(Continued)

(52) U.S. Cl.
CPC ............... *E02D 1/02* (2013.01); *E02D 1/022* (2013.01); *F16L 37/2445* (2013.01); *G01N 3/42* (2013.01); *G01N 33/24* (2013.01)

(58) Field of Classification Search
CPC ..... F16L 3/01; F16L 3/015; F16L 3/16; E02D 1/02
See application file for complete search history.

(56) References Cited

U.S. PATENT DOCUMENTS 4,063,830 A * 12/1977 Ban .................... E04H 15/60
135/114
6,062,090 A * 5/2000 Bachhuber .......... E02D 1/022
73/784
(Continued)

FOREIGN PATENT DOCUMENTS

EP 0989240 A1 3/2000
NL 1010459 C1 7/2000
WO 00/17481 A1 3/2000

OTHER PUBLICATIONS

Netherlands Patent Office, Search Report in NL 2014659, dated Nov. 25, 2015.
(Continued)

*Primary Examiner* — Son T Le
*Assistant Examiner* — Herbert K Roberts
(74) *Attorney, Agent, or Firm* — Hoffmann & Baron, LLP

(57) ABSTRACT

A soil probing device for determining properties of soil during penetration into ground using a soil probing device. The soil probing device has a measuring probe, a plurality of rod sections each having a central axis for assembly of the probing rod, driving means for penetrating the probing rod into the ground, and a measuring means for determining properties of the ground during penetration of the probing rod into the ground. The probing rod while penetrated into the ground is extendable each time by a new one of the rod sections. Each of the rod sections are provided at their outer ends with complementary male and female locking parts which in an axially aligned position of adjacent rod sections, are movable relative to each other from an unlocked into a locked position and from the locked position into the unlocked position.

16 Claims, 9 Drawing Sheets

(51) Int. Cl.
*G01N 3/42* (2006.01)
*G01N 33/24* (2006.01)

(56) References Cited

U.S. PATENT DOCUMENTS

| | | | |
|---|---|---|---|
| 2005/0120813 A1* | 6/2005 | Clark | E02D 1/06 |
| | | | 73/866.5 |
| 2014/0090674 A1* | 4/2014 | Thomas | E21B 37/00 |
| | | | 134/166 C |
| 2014/0216735 A1* | 8/2014 | Bell | E21B 19/22 |
| | | | 166/255.1 |
| 2014/0284921 A1 | 9/2014 | van der Valk | |

OTHER PUBLICATIONS

Netherlands Patent Office, Written Opinion in NL 2014659, dated Nov. 25, 2015.

* cited by examiner

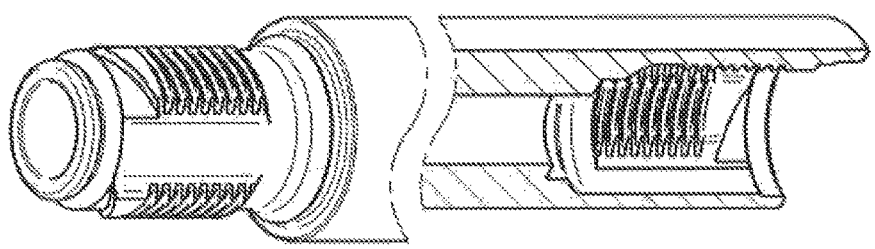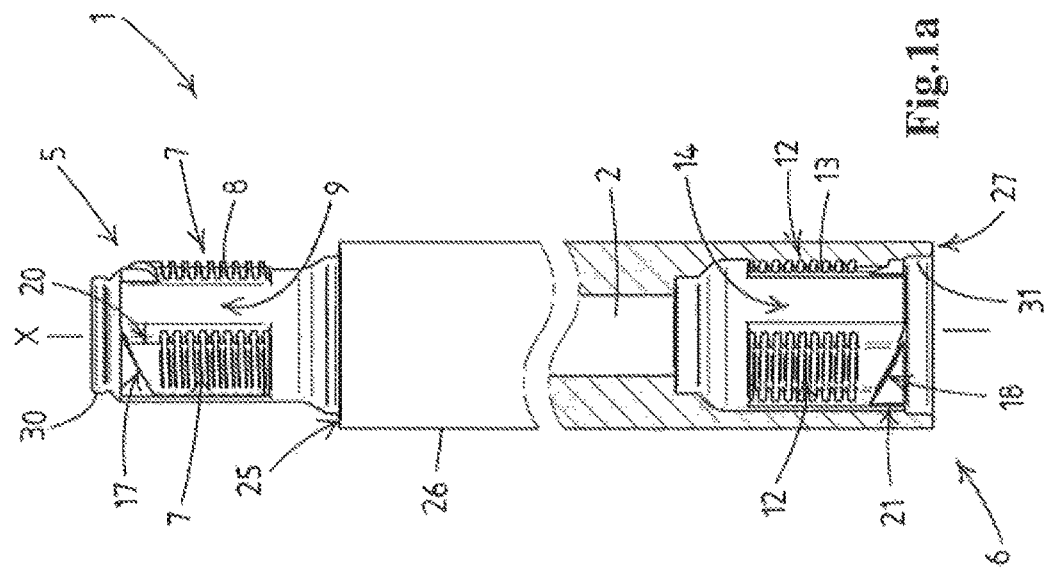

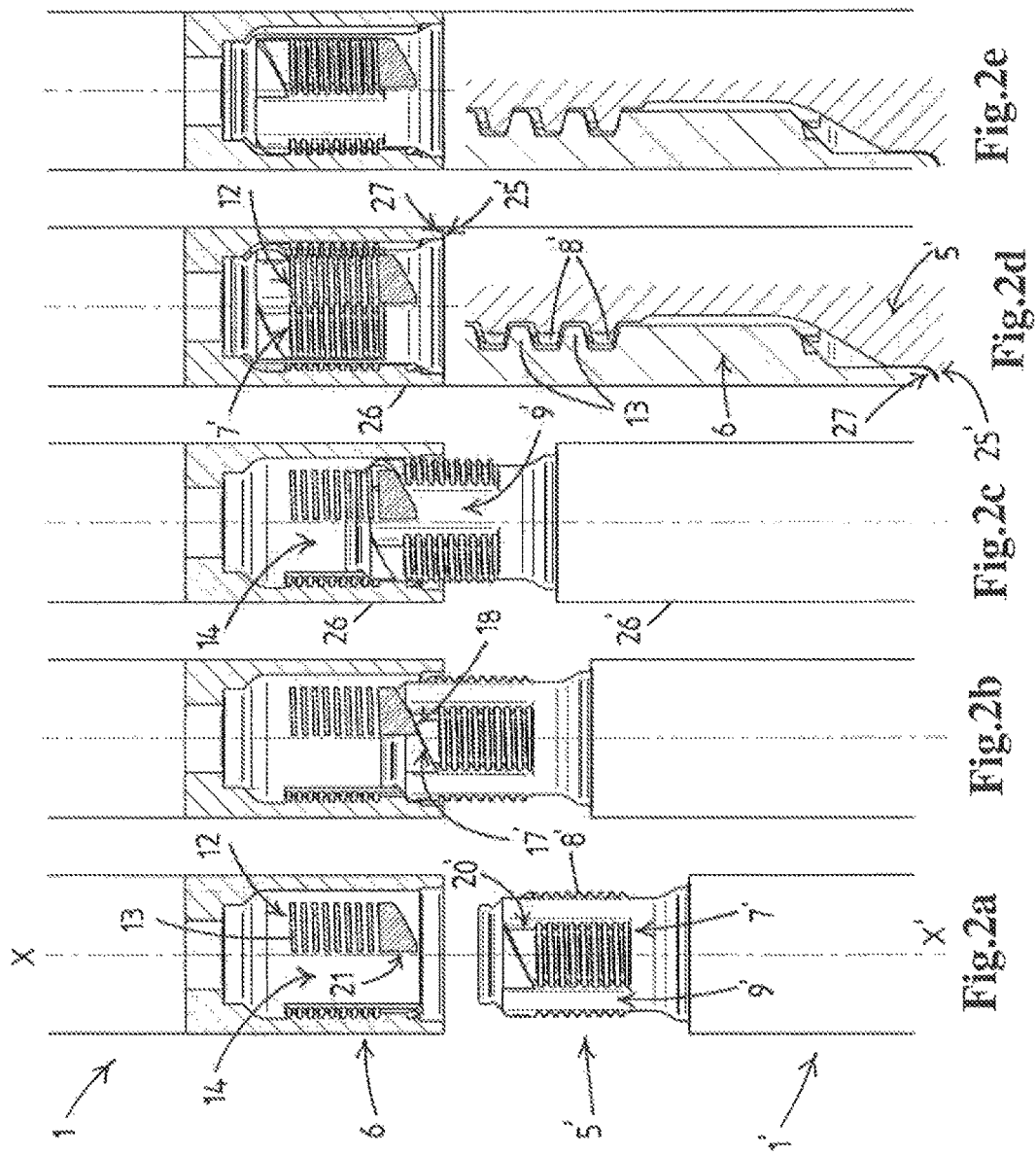

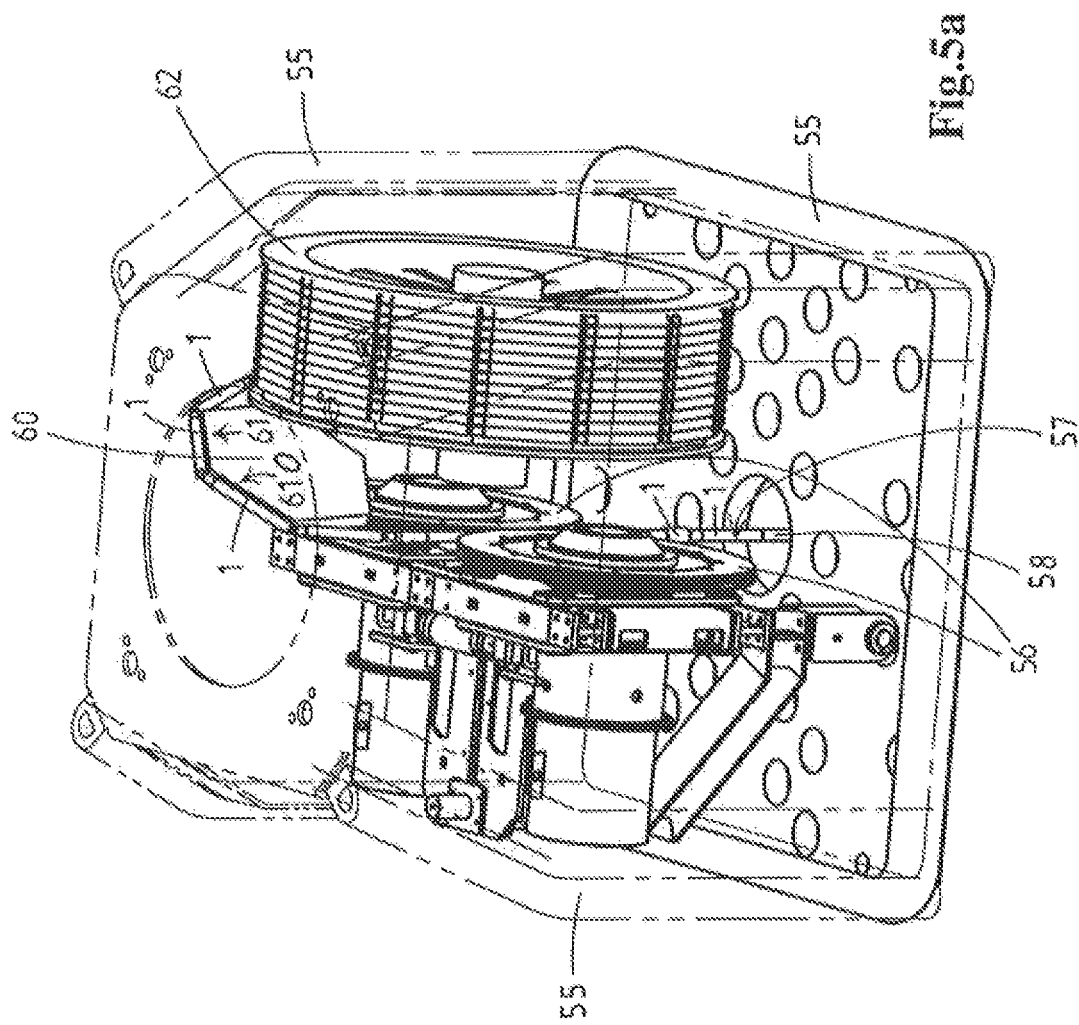

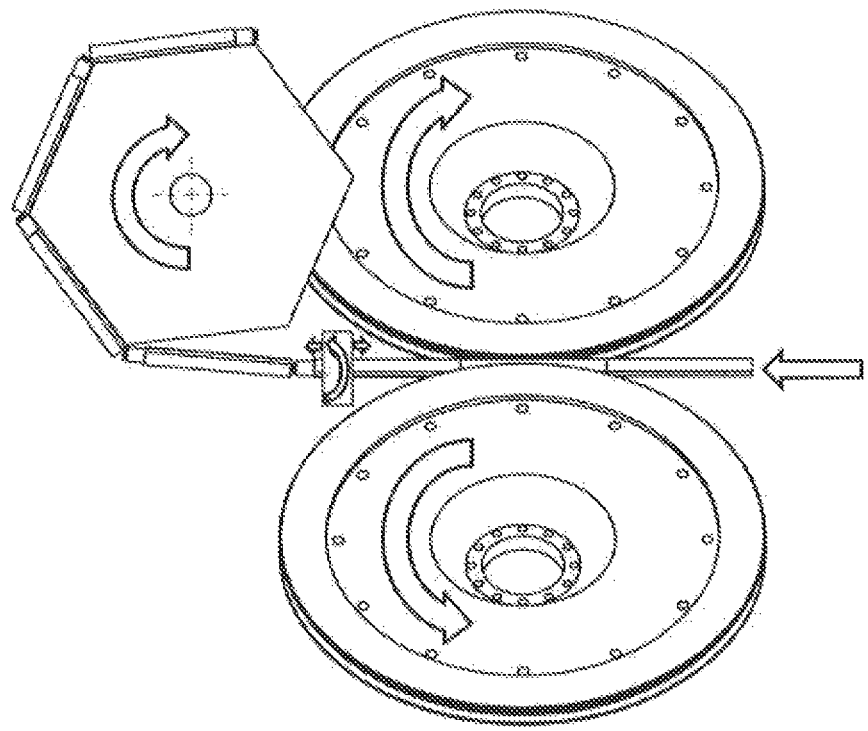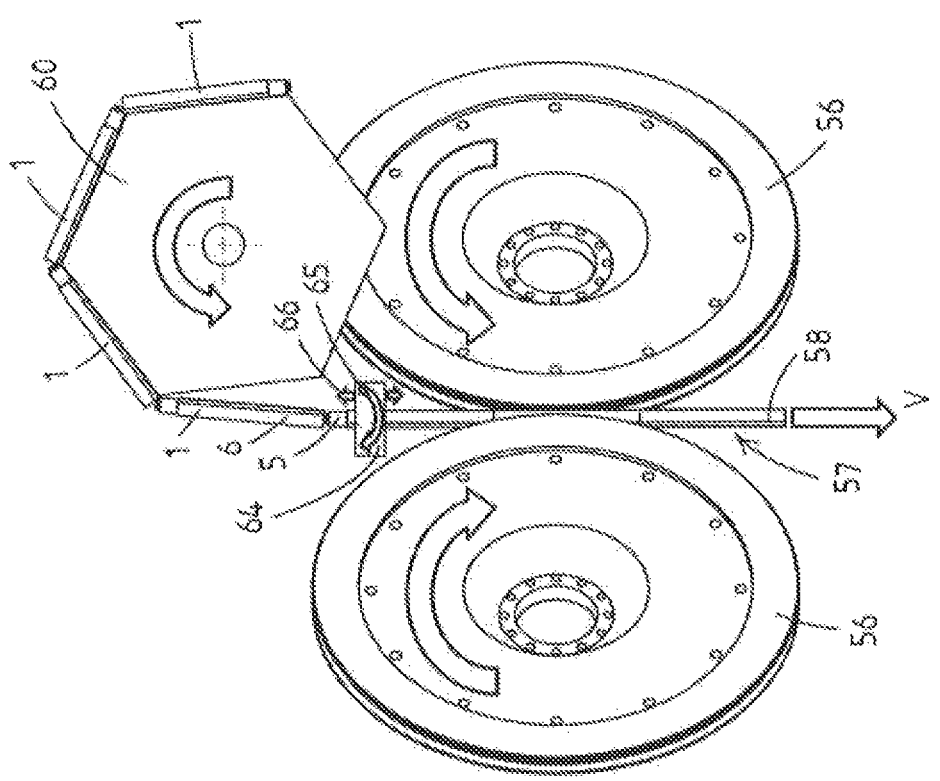

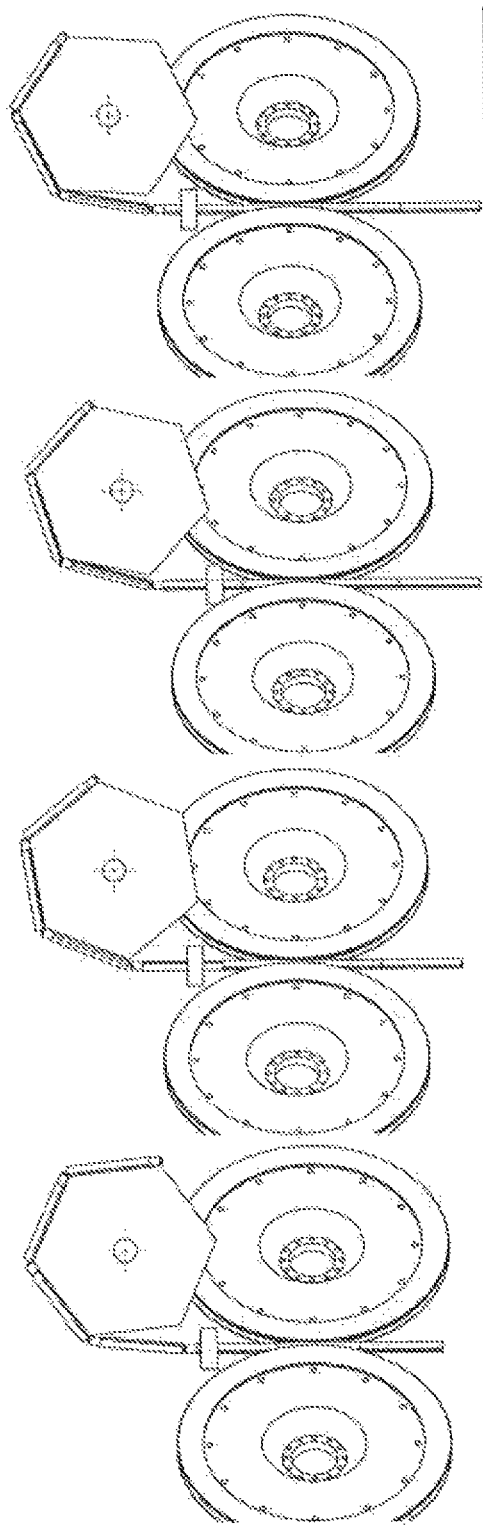

SOIL PROBING DEVICE HAVING A STRING OF FLEXIBLY CONNECTED ROD SECTIONS

CROSS-REFERENCE TO RELATED APPLICATIONS

This application claims the benefit of Netherlands Application No. NL 2014659, filed Apr. 17, 2015, the contents of which is incorporated by reference herein.

FIELD OF THE INVENTION

The present invention relates to the field of soil probing devices for determining geophysical and geotechnical properties of soil during penetration of a probing rod into the ground at land or at sea floors.

BACKGROUND OF THE INVENTION

Soil probing devices are known in various embodiments. For example EP 0 989 240, that was filed in the name of the present applicant, shows a soil probing device that has two sets of clamping members that can be moved up and down independently from each other and that are designed to alternately clamp a probing rod and push it gradually into the ground. Cone penetration measurements are performed during this penetration for determining the desired geophysical and geotechnical properties of the soil. The soil probing device can be supported directly onto a piece of land via a frame or can be mounted on a vehicle like a caterpillar-type. It can also be used for carrying out penetration measurements underwater, for example on a sea bed, provided that it is equipped with a special underwater drive unit. During penetration, the two sets of clamping members are controlled such that a first one of them gets moved down in a clamping position while taking the probing rod with it and pushing it into the ground, whereas a second one at the same time gets moved up along the probing rod in a release position. As soon as the first clamping set starts to reach its lowermost position, both clamping sets are controlled to switch functionality, that is to say that the second one then takes over the clamping of the probing rod and starts to push it further down into the ground, while the first one gets moved up along the probing rod in a release position. Thus the probing rod can be pushed in one continuous go into the ground. The probing rod here is formed by a measuring probe at its forward end and a plurality of distinctive straight rod sections of limited length that get connected thereto. With this, the rod sections are connected to one another by means of engageable male and female screw thread connections that are provided at free outer ends of the rods.

A disadvantage with this known device is that the picking and placing of new rod sections and screwing them onto the probing rod is time-consuming and difficult to automate, particularly when it is desired to perform the screwing of a new rod section to the probing rod at the same time that this probing rod is forced to penetrate at a constant speed into the ground in one continuous go. Another disadvantage is that the device requires a lot of space and that it may occur that one accidentally tries to place a new one of the rod sections onto the probing rod while this new rod section is wrongly positioned with its male and female locking parts. Yet another disadvantage is that during a removing of the probing rod out of the ground again, the unscrewing of the rod sections and then placing them in a storage facility also is time-consuming and difficult to automate Another known soil probing device that has been successfully commercialized for several years in the market by applicant under the trademark "Roson[,]" comprises a frame inside which two rotatable gripping wheels are provided as drive means. Those gripping wheels are positioned opposite one another. A probing rod is guided with a tight fit in between the gripping wheels. A rotating of the gripping wheels then forces the probing rod to penetrate in one continuous go into the ground. When to be used offshore for measurements on sea floors, it is known for this device to preassemble lengths of probing rod of up to 40 meters out of a plurality of rod sections inside an evenly long support mast that is placed upright on deck of or on-board of a ship. Subsequently the soil probing device together with the support mast and the preassembled length of probing rod inside it, gets lowered to the sea floor and there can start to perform a penetration test.

A disadvantage with this is that the preassembling of the probing rod on the ship is time-consuming and makes the operational costs for the ship expensive. Furthermore the preassembling process of the probing rod is sensitive for weather conditions and swells. Also the assembly of the preassembled probing rod and support mast is vulnerable because of its great length, not only during the preassembly process itself but also during its lowering towards the sea floor, which can be more than 2000 meters below. Further is disadvantageous that a heavy winch is needed for lowering the assembly to the sea floor, while at the same time means need to be provided for keeping the support mast and the preassembled probing rod in an upright position.

WO 00/17481 tries to overcome those disadvantages by no longer making use of distinctive straight rod sections, but by making use of a semi-rigid elongate probing rod that is wound in one piece onto a large diameter storage wheel. During penetration the elongate probing rod then can be gradually unwound from the wheel and forced to penetrate into the ground by suitable drive means, that here are formed by endless caterpillar-like engaging elements.

A disadvantage with this however is that the probing rod during its unwinding of the large diameter storage wheel needs to be plastically deformed such that it gets straight. When the penetration process is completed, and the probing rod needs to be pulled out of the ground, the probing rod again needs to be plastically deformed such that it can be wound back again on the large diameter storage wheel. Those repeated plastic deformations make it necessary to have the probing rod replaced after a limited number of usages. This makes this type of soil probing device costly. Another disadvantage is that the required plastic deformation makes it necessary to use a relative slender elongate probing rod, because otherwise the plastic deformation would become too difficult. In particular, with this type of elongate probing rod in one piece, a diameter of 19 mm is known to be used, whereas for probing rods composed out of distinctive rod sections, on almost twice as large diameter of 36 mm is more common However such a relative slender probing rod has limited strength and limits the maximum penetration depth. Also it entails the risk that it may start to plastically deform and deviate from its aimed vertical penetration path when running against obstacles.

SUMMARY OF THE INVENTION

The present invention aims to overcome those disadvantages at least partly and/or to provide a usable alternative. In particular the present invention aims to provide a user-friendly and cost-efficient soil probing device that can be used even at great depths under sea level, where it is hardly possible for operators or maintenance personnel to perform actions to the device like (dis)connecting blocked probing rod sections or trying to solve other types of malfunctions.

This aim is achieved by a soil probing device as disclosed herein. The device comprises a measuring probe and a plurality of rod sections for the assembly of a probing rod. Driving means are provided for penetrating the probing rod into the ground. During its penetrating into the ground, the probing rod is extendable each time by a new one of the rod sections. Measuring means are provided for determining properties of the ground during this penetration. The rod sections are provided at their outer ends with complementary male and female locking parts. In an axially aligned position of adjacent rod sections, those locking parts are movable relative to each other from an unlocked into a locked position and vice versa. According to the present invention, the adjacent rod sections furthermore are flexibly connected with each other by means of a flexible connection organ that allows the adjacent rod sections, in the unlocked position of their locking parts, to be flexibly moveable from a non-aligned storage position into said axially aligned position and vice versa.

This advantageously makes it possible for the new rod sections to be quickly and easily handled during their connection process to the probing rod. The new rod section can no longer get wrongly positioned with its lower locking part relative to the upper locking part of the probing rod. Owing to the flexible string connection the relative positions of their locking parts can always be guaranteed to be correct. Another advantage is that the process for feeding the new rod section towards the probing rod and subsequently positioning and connecting it thereto, can be automated in a far more simple manner. A pick and place unit for each time picking or placing a new rod section out of or into a storage facility is no longer necessary. The feeding of the rod sections to and from such a storage facility can now be attained by means of a simple pulling or pushing action. Owing to the flexible connections, a storage facility for the string of flexibly connected rod sections can even be positioned sideways of the driving means if desired, because of the flexibly connected rod sections being able to, in the unlocked positions of their locking parts, follow a semi-curved path thereto. This makes it possible to make the device compact and for example place it inside a relative slender protective frame, that makes the device less vulnerable to getting damaged. Penetration depths of more than 20 meters, and in particular of more than 40 meters can easily be reached and are no longer dependent on first having to preassemble the entire probing rod while using an evenly long support mast. This is particularly advantageous for offshore purposes at deep seas, because the device can simply be lowered to the sea floor, is there immediately ready for use, and does not need divers to operate.

In a preferred embodiment the flexible connection organ further can be designed to allow the new one of the rod sections to be rotatable around its central axis relative to the probing rod in said axially aligned position. This advantageously makes it possible to use locking parts of a type that need rotational alignment before being lockable together, like bayonet-type locking parts, and/or of a type that need rotational movement for locking them together, like screw thread-type locking parts.

In a further preferred embodiment the flexible connection organ further can be designed to allow the new one of the rod sections to be slidable with its lower locking part into and out of an upper locking part of the probing rod in the axially aligned position. This makes it possible to use locking parts of a type that need a sliding movement into each other for locking them together, like bayonet-type locking parts.

The flexible connection organ can for example be formed by a hinge connection that has its hinge axis extend perpendicular to the central axes of the adjacent rod sections, that is rotatable around at least one of the central axes of the adjacent rod sections, and that is slidable into and out of at least one of the adjacent rod sections along its central axis. The flexible connection organ can also be formed by a flexible elongate organ like a wire, cable, cord or the like.

Preferably, the flexible connection organ may comprise an elastically deformable part. In this way the connection organ is able to easily follow any required flexing or bending movements from its non-aligned storage position towards its axially aligned position relative to the probing rod.

Advantageously the elastically deformable part can be formed by a coil spring. Such a coil spring, for example made out of metal, is well able to deal with all the different types of forces that may get exerted upon the rod sections during positioning, connecting, disconnecting, moving from and towards a storage facility, etc. Not only can a length of the coil spring easily be changed, it is also able to flex or bend sideways and allow rotational movements. Furthermore it is able to transfer pulling and pushing forces.

In particular the coil spring can be freely rotatably connected to one or both of its adjacent rod sections. Thus during a rotational movement of the new rod section around its central axis relative to the probing rod, the windings of the coil spring do not have to be coiled tighter or looser.

More in particular the coil spring can be freely slidable in an axial inward direction inside a hollow channel or the like of one or both of its adjacent rod sections. Thus during an insertion of the locking parts into each other, the coil spring is able to swiftly move along in the axial direction without having to be largely compressed.

In another variant the entire rod sections including their locking parts can be hollow and a measurement cable can extend through the hollow rod sections and through the coil spring towards the measurement probe. The coil spring then forms a reliable protection for the measurement cable at its most vulnerable point in between the adjacent rod sections in the unlocked position of their locking parts.

The string of flexibly connected unlocked rod sections can for example be stored in a storage space where they can come to lie parallel upon and/or besides one another in for example fully bent or kinked positions. Preferably, however, a storage wheel is provided upstream of the driving means for winding the string of flexibly connected unlocked rod sections upon. The storage wheel then makes it possible to wind or unwind the string thereupon in a reliable and quick manner, with the straight rod sections being flexibly angled relative to each other depending on an available winding diameter on the winding wheel which may change in dependence of an amount of string that has already been wound upon it.

The storage wheel can advantageously be driven to exert a constant pushing or pulling force onto the string such that it is able to flexibly follow the movements that are imposed downstream on the probing rod by the driving means. The driving means themselves then can for example advantageously be driven to push the probing rod at a constant penetration speed into the ground.

In an embodiment a sprocket wheel may be provided upstream of the driving means, which sprocket wheel comprises a plurality of supporting segments around its circumference, preferably one supporting segment per rod section.

The sprocket wheel then can have respective ones of the flexibly connected rod sections engaging to its segments in such a way that they are able to exert a pushing or pulling force on the string of flexibly connected rod sections. During penetration, a pushing force can be exerted by the sprocket wheel upon the string in order to cause a new rod section to automatically move towards its aimed axially aligned position relative to the probing rod from where their locking parts can be locked together. During removing of the probing rod out of the ground, a pulling force can be exerted by the sprocket wheel in order to cause the uppermost rod section, after being unlocked from the probing rod, to automatically move towards its non-aligned storage position. The sprocket wheel segments can for example be formed by flat support faces, in which hook-shaped transitions between those flat support surfaces engage into transitions between the adjacent rod sections where the flexible connection organ also extends.

In a further embodiment an interspacing can be provided in between the sprocket wheel and the driving means, which interspacing is dimensioned for at least housing therein an upper locking part of the probing rod, the new one of the rod sections that is to be locked with the probing rod, as well as a lower locking part of yet another new rod section. Thus the new one of the rod sections that is to be connected to the probing rod, can each time temporarily take in a "floating" position in between the sprocket wheel and the driving means in which it is not locked yet to the probing rod such that it is able to freely move from its non-aligned storage position towards its axially aligned position, from where it can subsequently be locked to the probing rod. With this the flexible connection gives a maximum freedom to move to the new rod section, such that it can be pushed towards its axially aligned position and/or onto the locking part of the probing rod or be pulled out of and/or towards its axially non-aligned position away from the locking part of the probing rod. The freedom to move, if necessary, also lets the new rod section rotate around its central axis to a rotationally aligned position during its moving towards its axially aligned position.

The sprocket wheel can advantageously be driven at constant tension to exert a constant pushing or pulling force onto the string such that it is able to flexibly follow the movements that are imposed downstream on the probing rod by the driving means. The driving means themselves then can for example advantageously be driven to push the probing rod at a constant penetration speed into the ground. This makes the control of the device very simple and reliable. No expensive and difficult synchronization mechanisms are necessary for this. The sprocket wheel is able to follow the preferably constant speed movement of the probing rod, as well as the moving of the locking parts into and out of each other during the locking and unlocking operations.

Rotational positions of the sprocket wheel can be monitored and sent to a control unit for determining penetration depth registration of the probing rod. Thus the penetration depth registration can reliably be monitored and no separate depth registration means are needed anymore. This is a particularly reliable way of registration of the penetration depth because no slip can occur at the location of the sprocket wheel owing to the positive engagement between the sprocket wheel and the rod sections. Should slip occur between the driving means and the probing rod then this can also be detected out of the rotational position of the sprocket wheel, and thus be used as an important signal for an overload of the driving means of the device during penetration.

Further advantageous embodiments are also discussed in more depth herein. The invention also relates to a method for determining properties of soil during penetration of a probing rod into the ground using a soil probing device, as further discussed herein.

BRIEF DESCRIPTION OF THE FIGURES

The invention shall be explained in further detail below with reference to the accompanying drawings, in which:

FIG. 1*a-b* show front and perspective partly cross-sectional views of an embodiment of a rod section with male and female locking parts for a soil probing device according to the invention.

FIG. 2*a-e* show subsequent connection steps of locking parts of adjacent ones of the rod sections of FIG. 1, with lower parts of FIG. 2*e-d* showing enlarged views of engaging screw thread sections of the locking parts.

FIG. 5*a-c* show schematic perspective drawings of an embodiment of the soil probing device according to the invention.

FIG. 7*a-b* shows driving means and a sprocket wheel of FIGS. 4 and 5 during penetration and removal of a probing rod.

FIG. 8*a-d* shows the use of a rotator during subsequent connection steps of a new one of the rod sections with the probing rod of FIGS. 5 and 6.

DETAILED DESCRIPTION OF THE INVENTION

Figure 3B:
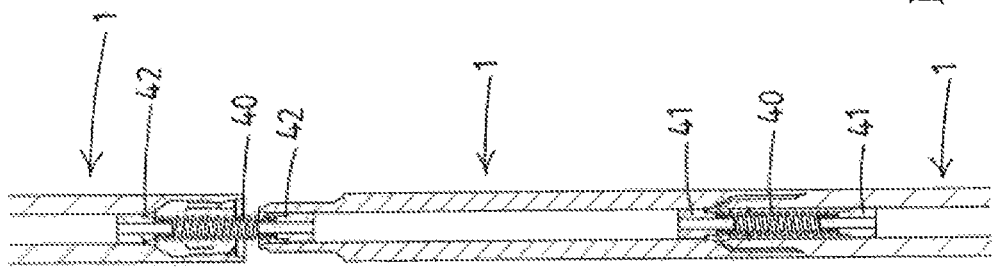
FIG. 3*a-b* show a string of flexibly connected ones of the rod sections of FIGS. 1 and 2 in subsequent phases of their connection steps.

In FIG. 1 a rod section for a probing rod is indicated in its entirety with the reference numeral 1. The rod section 1 is formed by a straight hollow tube that delimits a hollow channel 2 with a central axis that extends in an axial direction x. The rod section 1 comprises a male locking part 5 at its upper free end and a complementary female locking part 6 at its lower free end. With this the hollow channel 2 extends through the entire rod including through both the locking parts 5, 6.

The male locking part 5 has a reduced outer diameter relative to the rest of the rod section 1 and comprises three spaced apart threaded male bayonet columns 7 that are equally divided around its circumference. Each column 7 comprises an array of a plurality of right-handed screw thread turn sections 8 that lie above one another in the axial direction x. Slit-shaped smooth spacings 9 lie in between the columns 7.

The female locking part 6 has an increased inner diameter relative to the rest of the channel 2 and comprises three spaced apart threaded male bayonet columns 12 that are equally divided around its circumference. Each column 12 comprises an array of a plurality of right-handed screw thread turn sections 13 that lie above one another in the axial direction x. Slit-shaped smooth spacings 14 lie in between the columns 12.

Each of the screw thread turn sections 8, 13 extends over less than one sixth of the circumference seen in a circumferential direction r. Each of the spacings 9, 14 extends over more than one sixth of the circumference seen in the circumferential direction r. Each of the screw thread turn sections 8, 13 has a pitch angle that lies between 0.5-2.5 degrees. The ridges of the screw thread turn sections 8, 13 are dimensioned smaller than the channels lying between them such that the ridges of one locking part fit with an axial play between the ridges of the other locking part (see also FIG. 2*d-e*). The axial play here is about one fifth of a pitch of the screw thread turn sections 8, 13.

The columns 7 and 12 comprise complementary male and female angled sliding faces 17, 18 at their outer head sides. Like the screw thread turn sections 8, 13, the angled sliding faces 17, 18 also extend over less than one sixth of the circumference and leave the slit-shaped spacings 9, 14 free between them. The angled sliding faces 17, 18 have a pitch angle that is larger than 15 degrees.

Each male angled sliding face 17 towards its front side, here seen in a right-handed locking direction of the circumferential direction r, is delimited by a stop edge 20. The stop edge 20 extends in the axial direction x in the axial prolongation of front side leading ends of the male screw thread turn sections 8.

Each female angled sliding face 18 towards its back side, again seen in the right-handed locking direction, is delimited by a stop edge 21. The stop edge 21 extends in the axial direction x in the axial prolongation of back side tail ends of the female screw thread turn sections 13. The male locking part 5 at its axial inward end comprises a limitation edge 25 that is formed by a radially extending transition wall part that extends between the male locking part 5 and an outer circumferential wall 26 of the rod section 1. The female locking part 6 at its axial outer end comprises a limitation edge 27 that is formed by a radially extending transition wall part that extends between the female locking part 6 and the outer circumferential wall 26 of the rod section 1. The male locking part 5 comprises a reduced cylindrical end portion 30 that fits with a radial play inside a widened cylindrical end portion 31 of the female locking part 6.

A connecting of the male and female lock parts 5, 6 of two adjacent ones of the rod sections 1 shall now be explained with reference to FIG. 2*a-e* which show subsequent steps thereof. In FIG. 2*a* a lower female locking part 6 of an upper rod section 1 and an upper male locking part 5' of a lower rod section 1' are shown spaced apart from each other but already brought in an axially aligned position in which their respective central axes x, x' lie in each other's prolongation.

In FIG. 2*b* the male locking part 5' has been pushed in the axial direction x to start inserting into the female locking part 6 until the angled sliding face 17' has come to lie against the angled sliding face 18.

In FIG. 2*c* it is shown that the male locking part 5' remains being pushed in the axial direction x to insert further into the female locking part 6. With this the sliding faces 17', 18 cause the male locking part 5' to rotate in the right-handed rotational direction r relative to the female locking part 6. This relative rotation continues until a rotationally aligned position has been reached. In this rotationally aligned position the threaded male bayonet columns 7' have come to lie exactly in line with the slit-shaped spacings 14 of the female locking part 6, while the threaded female bayonet columns 12 have come to exactly lie in line with the slit-shaped spacings 9' of the male locking part 5. It is noted that owing to the provision of the stop edges 20, 21 it is prevented that the male locking part 5' accidentally may get rotated past by the rotationally aligned position, because leading ends of the screw thread turn sections 8', 13 abutting against respective ones of the stop edges 20, 21.

In FIG. 2*d* it is shown that a fully inserted position of the male locking part 5' inside the female locking part 6 has been reached owing to the continued exerting of the pushing force in the axial direction x. In this fully inserted position the limitation edges 25', 27 have come to lie against each other such that a further inserting is not possible. The outer circumferential walls 26, 26' of the adjacent rod sections 1, 1' then form one continuous smooth wall, without any stepped transitions. Furthermore, in this fully inserted position, the threaded male bayonet columns 7' have come to lie in the slit-shaped spacings 14 of the female locking part 6 in between the threaded female bayonet columns 12 of the female locking part 6, whereas those threaded female bayonet columns 12 themselves have come to lie in the slit-shaped spacings 9' in between the threaded male bayonet columns 7' of the male locking part 5'.

It can be seen in the enlarged lower part of FIG. 2*d* that in the shown fully inserted position, the screw thread ridges of the male screw thread sections 8' lie with axial play in front of screw thread channels in between the screw thread ridges of the female screw thread sections 13, and vice versa.

In FIG. 2*e* it is shown that, as a final connection step, the male locking part 5' is rotated in the right-handed rotational direction over an angle of approximately 60 degrees into the locked position. In this locked position each of the respective male and female screw thread turn sections 8', 13 have simultaneously fully engaged into each other.

Owing to the provided axial play, during a first part of this engagement rotation, lower side walls of the screw thread ridges of the male and female screw thread turn sections 8', 13 do not come to lie against each other, but merely start to axially move towards one another until the entire axial play between them is consumed. Then during a second part of the engagement rotation, the lower side walls of the screw thread ridges as well as the abutting limitation edges 25', 27 shall be pulled progressively tighter against each other. This can be seen in the enlarged lower part of FIG. 2*e*.

If it is desired to disconnect the rod sections from each other during a pulling of the probing rod out of the ground again, then the above steps can be performed in the opposite direction, that is to say first performing a rotational left-handed rotation over an angle of approximately 60 degrees until trailing ends of the screw thread turn sections come to abut against respective ones of the stop edges, and then pulling the male and female locking parts out of each other in the axial direction.

Figure 3A:
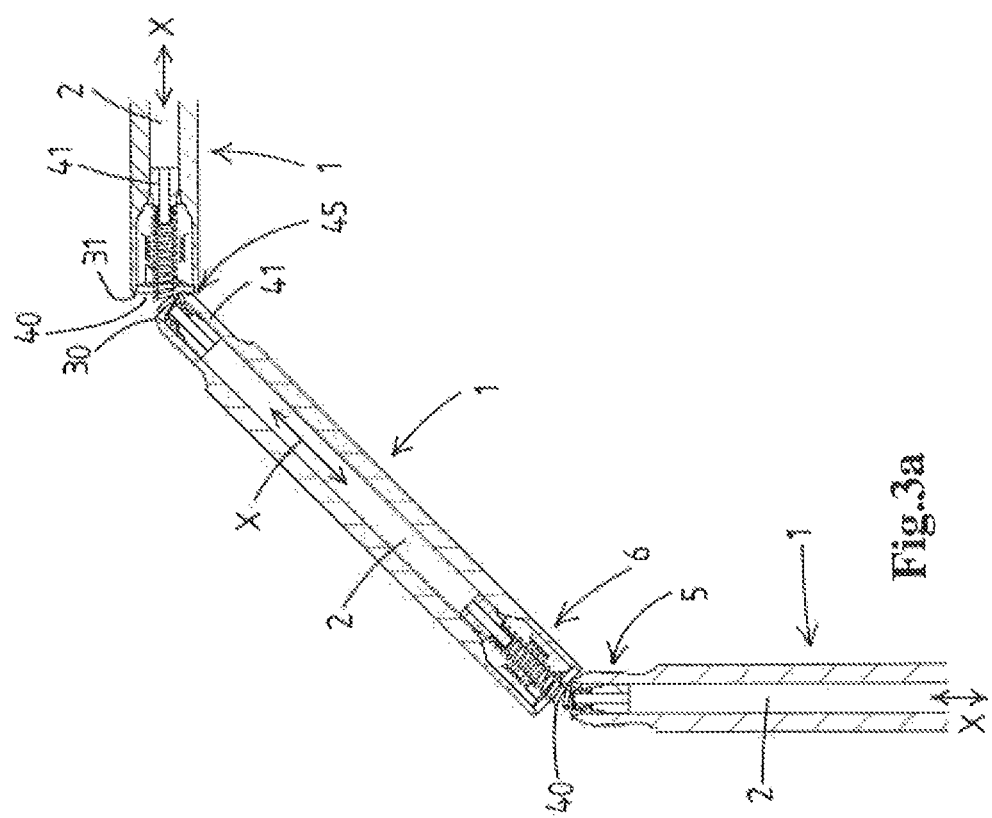

In FIG. 3*a-b* it is shown that adjacent ones of the rod sections 1 together form a flexible string by being connected to each other by means of flexible connection organs that here are formed by coil springs 40. Each coil spring 40 extends through a respective one of the male and female locking parts 5, 6. The outer ends of the coil spring 40 are connected to pistons 41 that are slidably and rotatably guided inside the cylinder-shaped channels 2. The pistons 41 are prevented from being pulled out of the channel 2 by means of inwardly projecting retainer organs 42 that are provided inside the channel 2.

As can be seen in FIG. 3*a* the coil springs 40 can be bend such that in the unlocked non-inserted position of the male and female locking parts 5, 6 of adjacent rod sections 1, those adjacent rod sections 1 are able to take non-aligned sideways bend positions relative to each other. In this non-aligned position the adjacent straight rod sections 1 can be angled relative to each other up to angles of 45 degrees or more. If desired it may even be possible for the rod sections 1 to come to lie parallel to each other.

In the angled position the coil spring 40 may have gotten stretched somewhat such that it exerts a slight bending/pulling force onto its adjacent rod sections 1 which tries to bend/pull the adjacent rod sections 1 towards the axially aligned position as is shown in the upper part of FIG. 3*b*. In this axially aligned position the male and female locking parts 5, 6 can easily and quickly be axially inserted into each other and then rotated relative to each other in order to reach their fully inserted locked position as can be seen in the lower part of FIG. 3*b*. During axial insertion of the locking parts 5, 6, one or both of the pistons 41 can follow this sliding movement by freely sliding inwards into the channels 2. If necessary the pistons 41 the can also perform the described alignment rotation by freely rotating inside the channels 2. During its locking rotation, one or both of the pistons 41 can follow this rotational movement by freely rotating inside the channels 2.

As can be seen in FIG. 3*a*, in the non-aligned positions, the widened cylindrical end portions 31 of the female locking parts 6 partly rest against the reduced cylindrical end portions 30 of the male locking parts 5 of their adjacent rod sections. This gives them ample play to already grip somewhat into each other while being able to bend/kink relative to each other from the non-aligned storage position towards the aligned position and vice versa. Together they form imaginary hinge points 45 for the adjacent rod sections 1. Furthermore, those end portions 30, 31 lying partly against each other in bend/kinked positions of the rod sections 1, make it possible to exert a pushing force onto the string of flexibly connected rod sections 1, which pushing force then can be transferred from one rod section 1 to the other along a line that extends through their respective central axes x.

Figure 4B:
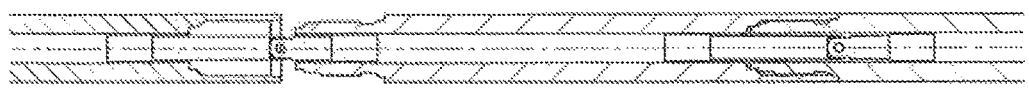
FIG. 4*a-b* show an alternative flexible connection for the string of FIG. 3.
Figure 4A:
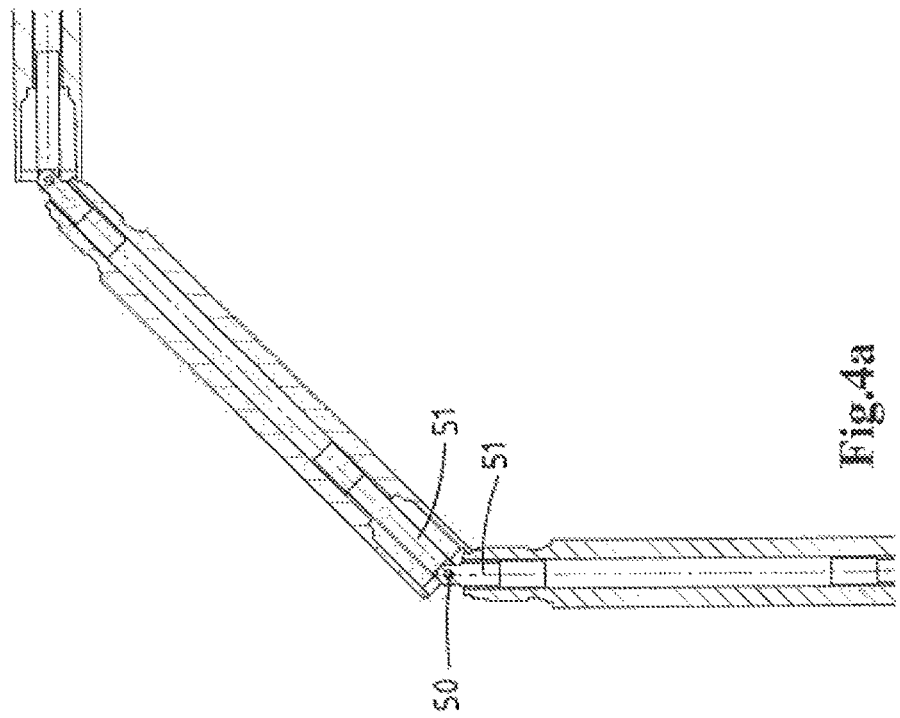

In FIG. 4*a-b* a variant is shown in which the flexible connection organs are formed by a hinge connection 50. The hinge connection 50 has a hinge axis that extends perpendicular to the central axes x of the adjacent rod sections 1. The hinge connection 50 is provided between pistons 51 that extend through the male and female locking parts 5, 6, and that are slidably and rotatably guided inside the cylinder-shaped channels 2. The pistons 51 are prevented from being pulled out of the channel 2 by means of suitable retainer organs that are provided inside the channel 2.

Figure 5C:
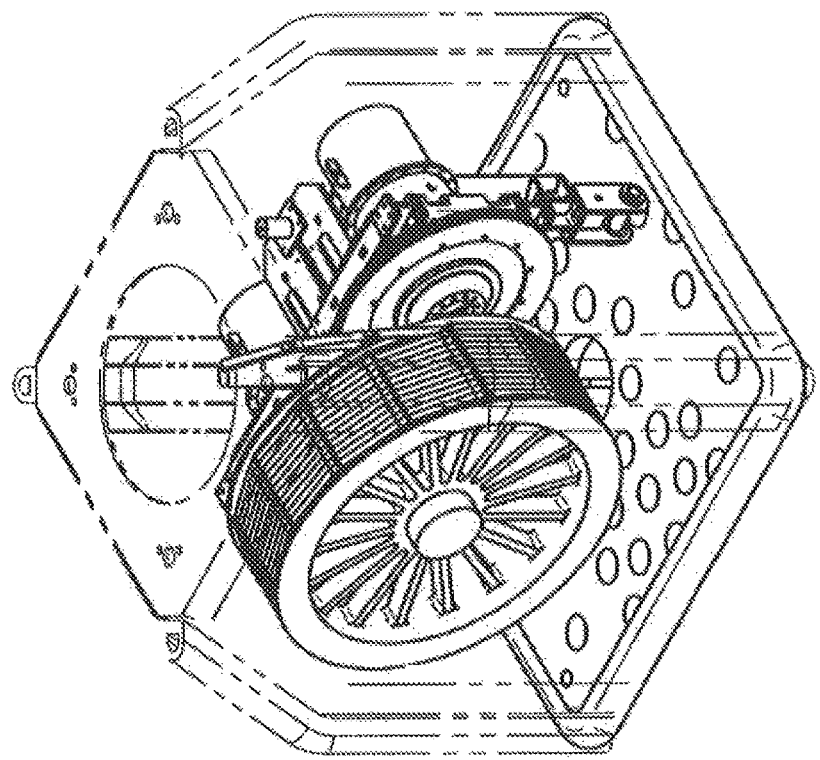
Figure 5B:
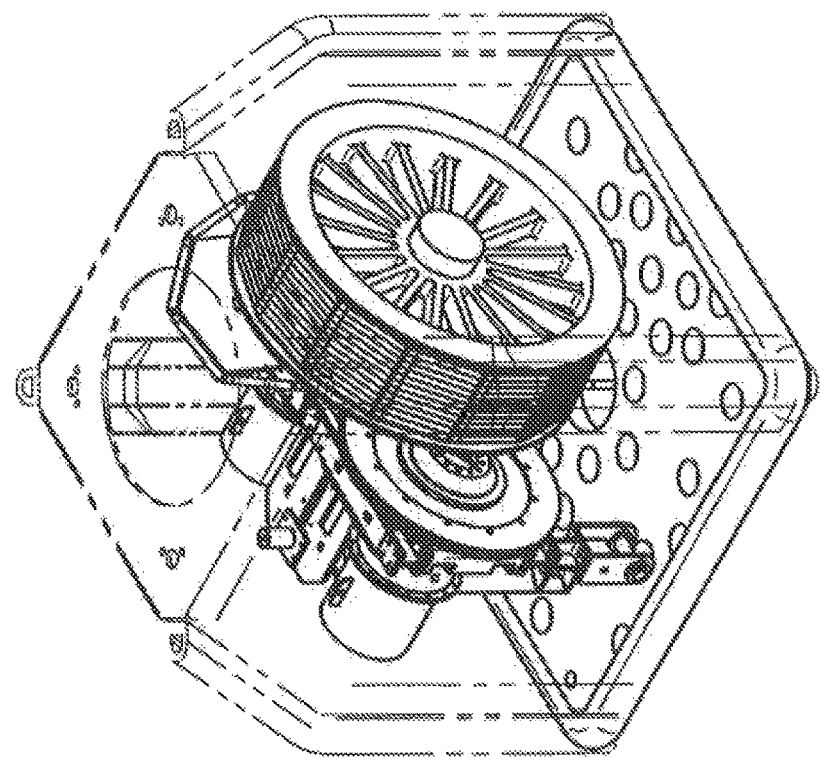
Figure 6B:
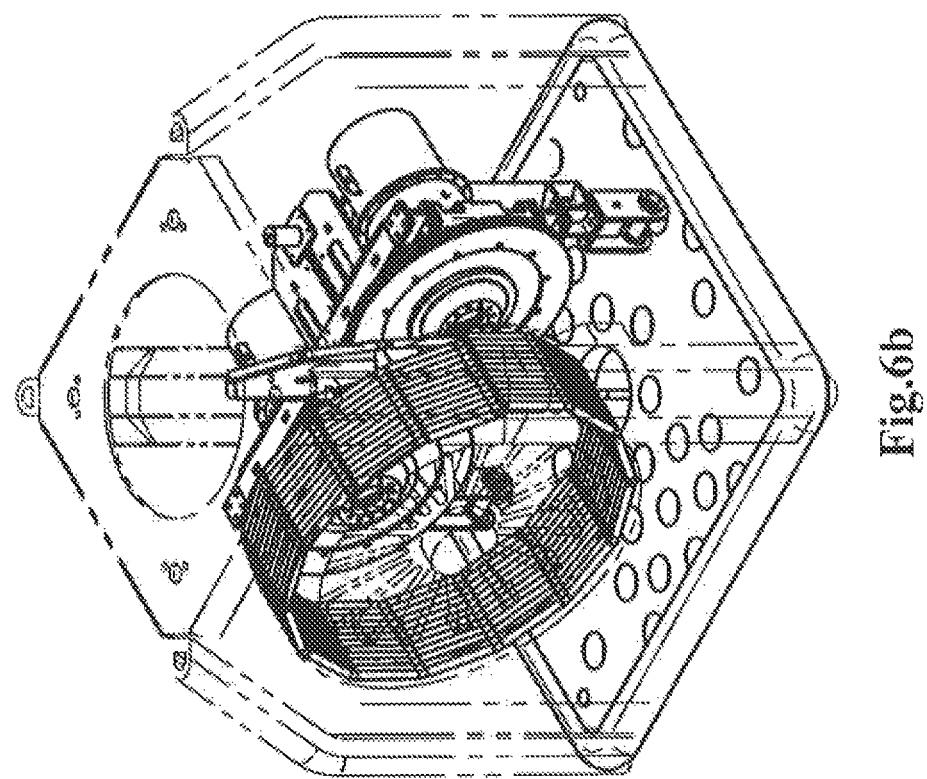
FIG. 6*a-b* are views according to FIG. 1*b-c* with part of a storage wheel of the device drawn with broken lines.
Figure 6A:
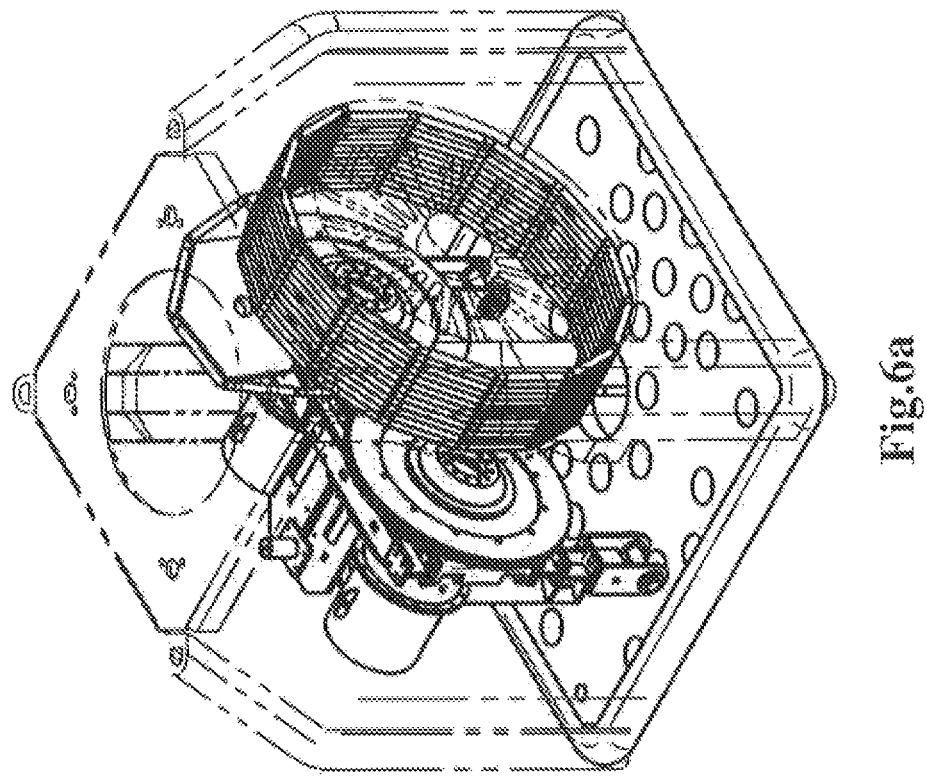

In FIGS. 5 and 6 an embodiment is shown of an entire soil probing device that makes use of the string of flexibly connected rod sections as shown in FIG. 3 or 4 including the male and female locking parts as shown in FIGS. 1 and 2.

The device is placed inside a frame 55 that can be placed onto a ground of which properties are to be determined, for example a sea floor. The device comprises two grooved rotatable gripping wheels 56 as driving means that are positioned opposite one another. A probing rod 57 having a measuring probe 58 at its lower end and a plurality of rod sections 1 already connected thereto, is guided with such a tight fit in between the gripping wheels 56, that a rotating of the gripping wheels 56 by means of a suitable drive unit, enables them to force the probing rod 57 to penetrate into the ground or to be pulled out of the ground again.

The measuring probe 58 can be connected via a measuring cable that extends through the plurality of rod sections 1 to a control unit (not shown). This control unit is designed for determining properties of the ground during penetration of the probe 58 into the ground. Penetration resistance forces that are active on the probe 58 during this penetration into the ground, and that may vary in dependence of the ground properties, are thus transmitted to the control unit. For example strain gauges can be provided inside or along the measuring probe 58 for measuring those forces. Instead of a measuring cable it is also possible to have the penetration resistance data get transmitted to the control unit wireless, for example via RF.

A sprocket wheel 60 is provided upstream of the wheels 56. The sprocket wheel 60 comprises six flat supporting segments 61. A string of unlocked non-aligned rod sections 1 is guided such over the sprocket wheel 60 that a rotating of the sprocket wheel 60 by means of a suitable drive unit, enables it to repeatedly push a lower locking part of a new one of the rod sections 1 of the string towards the probing rod 57 or to pull it away from it.

The sprocket wheel 60 is provided at a fixed relative distance from the gripping wheels 56 such that space is given therebetween for an upper part of the last rod section 1 that has already been locked to the probing rod 57 but that still extends above the gripping wheels 56, as well as to a new rod section 1 that extends freely unlocked in between the gripping wheels 56 and the sprocket wheel 60, as well as to part of yet another new rod section 1 of the string while it is still partly supported by the sprocket wheel 60 (see also FIG. 7). The freely extending unlocked rod section 1 thus has enough space to gradually bend/kink and rotate from its non-aligned angled position towards its aligned position to then get locked onto the probing rod 57.

A storage wheel 62 is provided upstream of the sprocket wheel 60 at a position sideways of the gripping wheels 56. The storage wheel 62 is formed by a reel having a relative large winding diameter. The string of unlocked angled rod sections 1 can be unwound from or wound upon the storage wheel 62 with distinctive turns of the string getting positioned side by side of each other. A total length of for example more than 50 meter of string can thus be stored onto the storage wheel 62. With this the storage wheel 62 gets rotated by means of a suitable drive unit. The sprocket wheel is supported with its rotation axis such that it is able to function as a level winder. For this it is able to hinge around a vertical axis. The storage wheel 62 is provided with a spiral groove for neatly taking up the respective string turns side by side.

The operation of the device shall now be explained with reference to FIG. 7 where merely the gripping wheels 56, the probing rod 57, the string of rod sections 1 and the sprocket wheel 60 of the device are shown.

In FIG. 7*a* it can be seen that the gripping wheels 56 are driven in opposite rotational directions. The driving takes place at a constant speed such that the probing rod 57 gets downwardly pushed at a constant speed v of for example a few centimeters per second. The clamping force that is exerted by the gripping wheels 56 onto the probing rod 57 is such that the chance of vertical slip is small while a chance for the probing rod 57 starting to rotate is neglectable. In FIG. 7*a* it can also be seen that the sprocket wheel 60 is driven in rotation. This driving however takes place at constant tension, such that the upstream string of rod sections 1 is able to follow the constant speed of the downstream probing rod 57 while at the same time accomplishing the required axial sliding of the lower locking part 6 of a new one of the rod sections 1 over the upper locking part 5 of the probing rod 57. Thus the sprocket wheel 60 functions as a pusher.

The device also comprises a rotator 64 that has merely been schematically indicated in FIG. 7. This rotator 64 is designed to give a rotational locking force to the new rod section 1 as soon as it is in the fully inserted position relative to the probing rod 57. The rotator 64 is designed to temporarily clamp the rod section 1 and force the locking rotation upon this rod section 1. This is indicated by the arrow 65. The rotator 64 at the same time performs a temporary downward movement at the same speed the probing rod 57 is moved down by the gripping wheels 56. This is indicated by the arrow 66.

FIG. 8a-d shows the progress of each time connecting a new rod section 1 to the probing rod 57 while it is moved towards and penetrated into the ground. It can be seen in FIG. 8b-c that when the rotator 64 screws a rod section 1 to the probing rod 57, the sprocket wheel 60 already starts to feed a new rod section 1. Also the up and down movement of the rotator 64 can be seen there.

During the entire penetration process, the rod sections 1, owing to their flexible connections, are well able to get transported from the storage wheel 62 via the sprocket wheel 60 towards the gripping wheels 56. The male and female locking parts 5, 6 are always in correct positions relative to each other, whereas the control of the various wheels of the device can be mainly passive by means of the driving at continuous speed or tension. Only the rotator 64 needs to be driven actively, for which the control information can come from a detection of the rotational position of the sprocket wheel 60 in combination with status information about the device whether it is resting, penetrating or retracting. With the aid of this position detection of the sprocket wheel 60, a control unit can permanently determine the position of the new rod section 1 that is present in the space between the gripping and sprocket wheels 56, 60, and then at preprogrammed positions activate the rotator 64 for starting to screw that rod section 1 onto the probing rod 57.

The device as shown in FIGS. 5 and 6 can not only be used for penetrating the probing rod 57 into the ground, it can also be used for pulling the probing rod 57 out of the ground again as soon as the penetration test has been completed. FIG. 7b shows the situation during such a retraction of the probing rod 57 out of the ground again. For this the driving directions of the various wheels and of the rotator are reversed. The gripping wheels 56 then preferably get driven at a higher reversed speed such that the probing rod 57 gets pulled out of the ground as quickly as possible. The rotator 64 then gets controlled to each time unscrew the uppermost rod section 1 of the probing rod 57, whereas the sprocket wheel 60 then pulls this unlocked rod section 1 out of its fully inserted position towards an angled non-aligned position. The string of unlocked rod sections 1 then gets guided by the sprocket wheel 60 towards the storage wheel 6 where it gets coiled around.

Besides the shown embodiments numerous variants are possible. For example the device can be placed permanently on a vehicle for performing penetration test on land instead of in a frame that needs to get positioned onto a piece of ground. It is also possible to use other types of driving means, like two sets of clamping members that can be moved up and down independently from each other and that are designed to alternately clamp a probing rod and push it gradually into the ground. Instead of having the probing rod get penetrated in one continuous go into the ground it is also possible to perform discontinuous penetration tests in which the driving means get stopped each time a new rod section needs to get connected thereto. Instead of a pusher and/or a rotator being provided, it is also possible to connect or disconnect the rod sections manually to or from the measuring probe. Instead of using the threaded bayonet-type of locking parts, it is also possible to use other types of locking parts, like for example uninterrupted male and female screw threaded locking parts that need to be screwed into each other by relative rotation over a plurality of turns, or by snap-fit locking parts that merely need to be axially inserted into each other or by non-threaded bayonet-type locking parts. Then also the flexible connections are already able to perform an advantageous role.

Thus the present invention advantageously is able to provide a reliable and efficiently operating soil probing device which makes use of a string of flexibly connected rod sections that can get quickly and automatically fed and rigidly connected to a probing rod while this rod is penetrating into the ground.

The invention claimed is:

1. A soil penetration test probing device comprising:
a measuring probe;
a plurality of rod sections each having a central axis for assembly of a probing rod, the probing rod further comprising the measuring probe;
driving means for penetrating the probing rod into the ground, the probing rod while penetrated into the ground extendable each time by a new one of the plurality of rod sections; and
a measuring means for determining geophysical and geotechnical properties of the ground during penetration of the probing rod into the ground, including for measuring penetration resistance forces that are active on the measuring probe of the probing rod during penetration into the ground,
wherein each of the rod sections are provided at their outer ends with complementary male and female locking parts that, in an axially aligned position of adjacent rod sections, are movable relative to each other from an unlocked into a locked position and from the locked position into the unlocked position,
wherein the adjacent rod sections are flexibly connected with each other by means of a flexible connection organ that allows the adjacent rod sections, in the unlocked position of the locking parts of each rod section, to be flexibly moveable from a non-aligned storage position into said axially aligned position and from the axially aligned position into the non-aligned storage position,
wherein a storage wheel is provided for winding the flexibly connected rod sections upon in the unlocked positions of their locking parts,
wherein a sprocket wheel is provided upstream of the driving means, which sprocket wheel comprises a plurality of segments around its circumference, the plurality of sprocket wheel segments having respective ones of the flexibly connected rod sections engaging thereto for exerting a pushing or a pulling force on the flexibly connected rod sections,
wherein an interspacing is provided in between the sprocket wheel and the driving means, which interspacing is dimensioned for at least one rod section as well as a male and a female locking part of upstream and downstream rod sections to fit in, and
wherein the driving means are drivable to push the probing rod at a constant speed into the ground, whereas the sprocket wheel is drivable to exert a constant pushing force onto the flexibly connected rod sections, such that the new one of the rod sections gets to follow the constant speed of the probing rod while at a same time moving the complementary male and female locking parts of the new one of the rod sections and of the probing rod towards their locked position.

2. The soil penetration test probing device according to claim 1, wherein the flexible connection organ further allows the new one of the rod sections to be rotatable around the central axis relative to the probing rod in said axially aligned position from the unlocked into the locked position.

3. The soil penetration test probing device according to claim 1, wherein the flexible connection organ further allows the new one of the rod sections to be slidable with a lower locking part into and out of an upper locking part of the probing rod in said axially aligned position from the unlocked into the locked position.

4. The soil penetration test probing device according to claim 1, wherein the flexible connection organ further comprises a hinge connection that has a hinge axis extend perpendicular to the central axes of the adjacent rod sections, that is rotatable around at least one of the central axes of the adjacent rod sections, and that is slidable into and out of at least one of the adjacent rod sections along the central axis from the unlocked into the locked position.

5. The soil penetration test probing device according to claim 1, wherein the flexible connection organ comprises an elastically deformable part.

6. The soil penetration test probing device according to claim 5, wherein the elastically deformable part is formed by a coil spring.

7. The soil penetration test probing device according to claim 6, wherein the coil spring is freely rotatably connected to at least one of its adjacent rod sections.

8. The soil penetration test probing device according to claim 6, wherein the rod sections are hollow and a measurement cable extends through the hollow rod sections and through the coil spring towards the measurement probe.

9. The soil penetration test probing device according to claim 1, wherein rotational positions of the sprocket wheel are monitored and sent to a control unit for determining a penetration depth registration of the probing rod.

10. The soil penetration test probing device according to claim 1, wherein the driving means comprise two rotatable gripping wheels that are positioned opposite one another with the probing rod being guided with a fit in between the gripping wheels, such that a rotating of the gripping wheels forces the probing rod to penetrate into the ground.

11. The soil penetration test probing device according to claim 1, further comprising a rotator that is provided in between the driving means and the sprocket wheel and that is designed to each time temporarily clamp the new one of the rod sections and to perform a downwards movement at the same constant speed as the probing rod while forcing a locking rotation upon the new one of the rod sections relative to the probing rod.

12. The soil penetration test probing device according to claim 11, wherein the male and female locking parts are screw threaded locking parts that are screwable into each other by relative rotation over a plurality of turns by means of the rotator.

13. The soil penetration test probing device according to claim 11, wherein the male and female locking parts are threaded-bayonet-type locking parts that are insertable into each other towards an inserted position by means of the constant pushing force exerted by the sprocket wheel and then rotatable relative to each other towards the locked position by means of the locking rotation forced upon by the rotator.

14. A soil penetration test probing device comprising:
a measuring probe;
a plurality of rod sections each having a central axis for assembly of a probing rod, the probing rod further comprising the measuring probe;
driving means for penetrating the probing rod into the ground, the probing rod while penetrated into the ground extendable each time by a new one of the plurality of rod sections; and
a measuring means for determining geophysical and geotechnical properties of the ground during penetration of the probing rod into the ground, including for measuring penetration resistance forces that are active on the measuring probe of the probing rod during penetration into the ground,
wherein each of the rod sections are provided at their outer ends with complementary male and female locking parts that, in an axially aligned position of adjacent rod sections, are movable relative to each other from an unlocked into a locked position and from the locked position into the unlocked position, and
further wherein the adjacent rod sections are flexibly connected with each other by means of a flexible connection organ that allows the adjacent rod sections, in the unlocked position of the locking parts of each rod section, to be flexibly moveable from a non-aligned storage position into said axially aligned position and from the axially aligned position into the non-aligned storage position,
wherein a sprocket wheel is provided upstream of the driving means, which sprocket wheel comprises a plurality of segments around its circumference, the plurality of sprocket wheel segments having respective ones of the flexibly connected rod sections engaging thereto for exerting a pushing or a pulling force on the flexibly connected rod sections, and
wherein the driving means are drivable to push the probing rod at a constant speed into the ground, whereas the sprocket wheel is drivable to exert a constant pushing force onto the flexibly connected rod sections, such that the new one of the rod sections gets to follow the constant speed of the probing rod while at a same time moving the complementary male and female locking parts of the new one of the rod sections and of the probing rod towards their locked position.

15. A method for performing soil penetration tests for determining geophysical and geotechnical properties of soil during penetration of a probing rod into ground using a soil penetration test probing device according to claim 14 comprising the steps of:
penetrating the probing rod into the ground, while extending the probing rod each time by a new one of a plurality of rod sections for assembly of the probing rod; and
determining by the probing rod the geophysical and geotechnical properties of the soil during penetration of the probing rod into the ground, including measuring penetration resistance forces that are active on a measuring probe of the probing rod during penetration into the ground;
wherein the rod sections are fed towards driving means as a string of flexibly connected rod sections, wherein the new one of the rod sections each time is moved from a non-aligned storage position into an axially aligned position with the probing rod, and
wherein the driving means push the probing rod at a constant speed into the ground, while the sprocket wheel exerts a constant pushing force onto the new one of the flexibly connected rod sections, such that this new one of the rod sections gets to follow the constant speed of the probing rod while at a same time moving the complementary male and female locking parts of the new one of the rod sections and of the probing rod towards their locked position.

16. A soil penetration test probing device comprising:
a measuring probe;
a plurality of rod sections each having a central axis for assembly of a probing rod, the probing rod further comprising the measuring probe;
driving means for penetrating the probing rod into the ground, the probing rod while penetrated into the ground extendable each time by a new one of the plurality of rod sections; and
a measuring means for determining geophysical and geotechnical properties of the ground during penetration of the probing rod into the ground, including for measuring penetration resistance forces that are active on the measuring probe of the probing rod during penetration into the ground,
wherein each of the rod sections are provided at their outer ends with complementary male and female locking parts that, in an axially aligned position of adjacent rod sections, are movable relative to each other from an unlocked into a locked position and from the locked position into the unlocked position, and
further wherein the adjacent rod sections are flexibly connected with each other by means of a flexible connection organ that allows the adjacent rod sections, in the unlocked position of the locking parts of each rod section, to be flexibly moveable from a non-aligned storage position into said axially aligned position and from the axially aligned position into the non-aligned storage position,
wherein a storage wheel is provided for winding the flexibly connected rod sections upon in the unlocked positions of their locking parts,
wherein a sprocket wheel is provided upstream of the driving means, which sprocket wheel comprises a plurality of segments around its circumference, the plurality of sprocket wheel segments having respective ones of the flexibly connected rod sections engaging thereto for exerting a pushing or a pulling force on the flexibly connected rod sections,
an interspacing is provided in between the sprocket wheel and the driving means, which interspacing is dimensioned for at least one rod section as well as a male and a female locking part of upstream and downstream rod sections to fit in.

* * * * *